United States Patent [19]
Spagnol et al.

[11] Patent Number: 6,013,840
[45] Date of Patent: Jan. 11, 2000

[54] PROCESS FOR THE ACYLATION OF AROMATIC ETHERS

[75] Inventors: Michel Spagnol, Lyons; Laurent Gilbert, Paris; Eric Benazzi, Montesson; Christian Marcilly, Houilles, all of France

[73] Assignee: Rhodia Chimie, Courbevoie, France

[21] Appl. No.: 08/765,533

[22] PCT Filed: May 10, 1996

[86] PCT No.: PCT/FR96/00716

§ 371 Date: Jan. 9, 1997

§ 102(e) Date: Jan. 9, 1997

[87] PCT Pub. No.: WO96/35655

PCT Pub. Date: Nov. 14, 1996

[30] Foreign Application Priority Data

May 12, 1995 [FR] France .................................. 95 05682

[51] Int. Cl.⁷ .................................................. C07C 45/00
[52] U.S. Cl. .......................................... 568/322; 568/337
[58] Field of Search .............................................. 568/322

[56] References Cited

U.S. PATENT DOCUMENTS

| | | | |
|---|---|---|---|
| 3,130,007 | 4/1964 | Breck ......................................... | 23/113 |
| 4,960,943 | 10/1990 | Botta et al. ............................... | 568/319 |
| 5,227,529 | 7/1993 | Neuber et al. ........................... | 568/319 |

FOREIGN PATENT DOCUMENTS

| | | | |
|---|---|---|---|
| 0 455 332 | 6/1991 | European Pat. Off. ........ | C07C 45/46 |
| 0 407 203 | 9/1991 | European Pat. Off. ......... | B01J 29/06 |
| 2 667 063 | 3/1992 | France ......................... | C07C 49/813 |

*Primary Examiner*—Paul J. Killos
*Attorney, Agent, or Firm*—John Daniel Wood

[57] ABSTRACT

The present invention concerns a process for the acylation of an aromatic ether.

Preferably the invention relates to a process for the acylation of a substituted aromatic ether, in particular veratrol.

The acylation process of the invention consists of reacting the ether with an acylation agent in the presence of a zeolitic catalyst, and is characterized in that the acylation reaction is carried out in the presence of an effective quantity of a catalyst comprising a faujasite type zeolite or a Y zeolite with the following physico-chemical characteristics:

an atomic ratio denoted "global $Si/Me^1$" between the number of atoms of the element silicon and the number of atoms of every trivalent element $Me^1$ contained in the zeolite in the range 2.4 to 90, preferably in the range 2.4 to 75, and more preferably in the range 2.4 to 60;

an $Me^2$ alkali metal content such that the atomic ratio $Me^2/Me^{1(IV)}$ between the number of atoms of alkali metal $Me^2$ and the number of atoms of every trivalent element $Me^{1(IV)}$ included in the zeolitic network is less than 0.2, preferably less than 0.1, and more preferably less than 0.05.

27 Claims, No Drawings

PROCESS FOR THE ACYLATION OF AROMATIC ETHERS

The present invention concerns is a process for the acylation of an aromatic ether.

Preferably, the invention relates to a process for the acylation of a substituted aromatic ether, more particularly veratrol.

The invention is applicable to the preparation of alkoxyaromatic alkylketones.

Conventional processes for the acylation of aromatic compounds, in particular the ethers of phenols, consist of carrying out a Friedel-Crafts acylation reaction.

The aromatic compound is reacted with an acylation agent in the presence of a catalyst which is generally aluminium chloride.

This type of process is illustrated by the work of C KURODA et al., [Sci. Papers Inst. Phys. Chem. Res. 18, pp 51–60 (1932)] which describes the preparation of methoxy-acetophenones by the reaction of an aromatic compound carrying 1 to 3 methoxy groups with acetyl chloride in the presence of aluminium chloride.

The use of aluminium chloride, however, has a number of disadvantages. Aluminium chloride is corrosive and an irritant. Further, a large quantity of aluminium chloride must be used, at least equal to the stoichiometric quantity, because of complexation with the ketone formed. As a result, the aluminium chloride is not a true catalyst.

At the end of the reaction, the aluminium chloride must be eliminated from the reaction medium by carrying out acidic or basic hydrolysis.

Hydrolysis implies the addition of water to the reaction medium, considerably complicating the process since the metal cation, and more particularly the aluminium cation, forms aluminium polyoxo- and/or polyhydroxo complexes of milky consistency, which are difficult to separate. This necessitates a long, expensive treatment following hydrolysis comprising extraction of the organic phase, separation of the aqueous and organic phases, and even drying of the latter. Separation of aluminium chloride is thus lengthy and expensive.

Further, there are problems with aqueous saline effluents which must then be neutralised and which necessitate an additional operation.

Still further, the aluminium chloride cannot be recycled as it has been hydrolysed.

In order to overcome this disadvantage, it has been suggested that the reaction be carried out in the presence of heterogeneous catalysts.

Thus for about a decade, the use of zeolites as acylation catalysts has been recommended.

Prins et al. described the acetylation of anisole by acetic anhydride [9th International Zeolite Congress—Montréal Congrès (1992)] in the presence of zeolites such as β zeolite or USY zeolite. It should be noted that β zeolites produced more interesting results as regards both the degree of conversion and the reaction yield.

European patent EP-A-0 279 322 disclosed a vapour phase reaction of an aromatic compound (veratrol) with a carboxylic acid derivative in the presence of a zeolite in its H form such as mordenite, faujasite and ZSM-5. However, the yield for the reaction of veratrol and p-chlorobenzoyl chloride mentioned in Example 1 was only 22%.

It appears that the use of zeolites as catalysts for a reaction using bulky molecules causes problems to the skilled person in that the sensitivity and yield of the reaction are not satisfactory.

An object of the present invention is to provide a process which can overcome the above disadvantages.

We have now discovered, and this constitutes an object of the present invention, a process for the acylation of an aromatic ether which consists of reacting the ether with an acylation agent in the presence of a zeolitic catalyst, the process being characterized in that the acylation reaction is carried out in the presence of an effective quantity of a catalyst comprising a faujasite type zeolite or a Y zeolite with the following physico-chemical characteristics:

an atomic ratio denoted "global $Si/Me^1$" between the number of atoms of the element silicon and the number of atoms of every trivalent element $Me^1$ contained in the zeolite in the range 2.4 to 90, preferably in the range 2.4 to 75, and more preferably in the range 2.4 to 60;

an $Me^2$ alkali metal content such that the atomic ratio $Me^2/Me^{1(IV)}$ between the number of atoms of alkali metal $Me^2$ and the number of atoms of every trivalent element $Me^{1(IV)}$ included in the zeolitic network is less than 0.2, preferably less than 0.1, and more preferably less than 0.05.

The term $Me^1$ denotes any element with a degree of oxidation of +3, in particular aluminium, gallium, iron, boron and mixtures thereof, preferably aluminium.

The term $Me^1$ denotes any metal selected from the group of elements in column 1a and mixtures thereof, preferably alkali metals such as lithium, sodium, potassium, rubidium and caesium. $Me^2$ preferably represents sodium or potassium.

The term $Me^{1(IV)}$ denotes any element with a degree of oxidation of +3, in particular aluminium, gallium, iron or boron and mixtures thereof, preferably aluminium, which is present in the zeolitic network.

Reference should be made to the periodic classification of the elements published in the "Bulletin de la Société Chimique de France", No 1 (1966) for the definition of the elements.

The faujasite type or Y zeolite which is preferably used has an atomic ratio denoted the "$Si/Me^{1(IV)}$ of the zeolitic framework" between the number of atoms of the element silicon and the number of atoms of every trivalent element $Me^{1(IV)}$ included in the zeolitic framework which is in the range 5 to 100, preferably in the range 6 to 80, and more preferably in the range 8 to 60.

The physico-chemical parameters which characterise the zeolite used in the process of the invention are determined using the methods given below.

The "global $Si/Me^{1(IV)}$" atomic ratio of the zeolite is primarily determined by X ray fluorescence.

The "$Si/Me^{1(IV)}$" atomic ratio of the zeolite framework is determined using a method which is known to the skilled person, for example, by X ray diffraction which, by measuring the lattice parameter of the zeolite, produces the $Si/Me^{1(IV)}$ ratio of the framework by applying the Fichtner-Schmittler relationship (H. Fichtler-Schmittler, U. Loshe, G. Engelhardt and V. Patzelova, V. Cryst. Rest. Tech. 1984, 1984, 19, K1), by $^{29}Si$ NMR of the solid, and by infrared spectroscopy.

The catalyst used in the process of the invention comprises an active phase which is a faujasite type or Y zeolite which has certain well defined characteristics. Thus it has a low content of element $Me^1$, which is preferably aluminium.

More precisely, in its dehydrated state, the Y zeolite or faujasite type zeolite has a chemical composition which corresponds to the following empirical formula:

where:

Me$^1$ and Me$^2$ have the meanings given above;

n, equal to the "global Si/Me$^1$" atomic ratio defined above, is in the range 2.4 to 90, preferably in the range 2.4 to 75, and more preferably in the range 2.4 to 60;

x, equal to the Me$^2$/Me$^{1(IV)}$ ratio defined above, is less than 0.2, preferably less than 0.1 and more preferably in the range 0 to 0.05.

The lattice parameter α of the zeolite used in the process of the invention is less than 24.50 Angström, preferably in the range 24.23 to 24.42 Angström.

Y and faujasite type zeolites are described in the literature [see "Atlas of zeolite structure types" by W. M. Meier and D. H. Olson published by the Structure Commission of the International Zeolite Association (1978), or U.S. Pat. No. 3,130,007].

In order to use a Y zeolite with the above characteristics, it may be necessary to dealuminise the zeolite so that the Si/Me$^1$ atomic ratios defined above are in the prescribed ranges.

Methods which are known to the skilled person can be used, non exhaustive examples of which are: calcining in the presence of vapour, calcining in the presence of steam followed by attack with mineral acids (HNO$_3$, HCl . . . ), direct dealuminising using reactants such as silicon tetrachloride (SiCl$_4$), ammonium hexafluorosilicate ((NH$_4$)$_2$SiF$_6$), or ethylenediaminetetraacetic acid (EDTA) and its mono- or disodium form. Dealuminising can also be carried out by direct acid attack with solutions of mineral acids such as hydrochloric acid, nitric acid, sulphuric acid or aromatic acids, in particular acetic acid or oxalic acid.

Any combination of the above dealuminising methods is also possible.

The zeolite constitutes the catalytic phase. It can be used alone or mixed with a mineral matrix. In this description, the term "catalyst" is used to denote a catalyst formed entirely of zeolite or a mixture with a matrix prepared using techniques which are known to the skilled person.

The matrix can be selected from metal oxides such as aluminium oxides, silicon oxides and/or zirconium oxides, or from clays, in particular kaolin, talc or montmorillonite.

The active phase in the catalyst represents 5% to 100% by weight of the catalyst.

The catalysts can be in different forms in the process of the invention: powder, formed products such as granules (for example extrudates or spherules) or pellets, obtained by extrusion, moulding, compacting or any other known process. Granules or spherules are used industrially as they have the most advantages as regards both efficiency and ease of use.

As mentioned above, the process of the invention is suitable for carrying out acylation of an aromatic ether, preferably a substituted aromatic ether.

In the following disclosure of the present invention, the term "aromatic ether" denotes an aromatic compound in which a hydrogen atom which is directly bonded to the aromatic nucleus is replaced by an ether group and the term "aromatic" denotes the conventional idea of aromaticity as defined in the literature, in particular Jerry MARCH, Advanced Organic Chemistry, 4th edition, John Wiley and Sons, 1992, pp.40 ff.

The term "substituted aromatic ether" denotes an aromatic ether containing at least one other substituent on the aromatic nucleus, preferably in the ortho position.

More precisely, the present invention provides a process for the acylation of an aromatic ether with general formula (I):

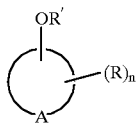

where:

A represents the residue of a cycle forming all or a portion of a monocyclic or polycyclic aromatic carbocyclic system containing at least one OR' group: the cyclic residue may carry one or more substitutents:

R represents one or more substitute which may be identical or different;

R' represents a hydrocarbon radical containing 1 to 24 carbon atoms, which may be a saturated or unsaturated, linear or branched acyclic aliphatic radical; a monocyclic or polycyclic, and saturated, unsaturated or aromatic cycloaliphatic radical; or a saturated or unsaturated, linear or branched aliphatic radical carrying a cyclic substitutent;

R' and R may form a cycle which may contain a further heteroatom;

n is a number less than or equal to 4.

For simplicity in the present text, the term "alkoxy groups" denotes R'—O— type groups where R' has the meaning given above. R' thus represents both a saturated, unsaturated or aromatic, acyclic or cycloaliphatic aliphatic radical and a saturated or unsaturated aliphatic radical carrying a cyclic substitutent.

The aromatic ether used in the process of the invention has formula (I) where R' represents a saturated or unsaturated, linear or branched acyclic aliphatic radical.

More preferably, R' represents a linear or branched alkyl radical containing 1 to 12 carbon atoms, preferably 1 to 6 carbon atoms: the hydrocarbon chain may be interrupted by a heteroatom (for example oxygen), by a functional group (for example —CO—) and/or may carry a substituent (for example a halogen).

The saturated or unsaturated, linear or branched acyclic aliphatic radical may carry a cyclic substitutent. The term cycle preferably denotes a saturated, unsaturated or aromatic carbocyclic cycle, preferably cycloaliphatic or aromatic, and in particular cycloaliphatic containing 6 carbon atoms in the cycle, or benzenic.

The acyclic aliphatic radical may be bonded to the cycle by a valence bond, a heteroatom or a functional group; examples are given above.

The cycle may optionally be substituted; examples of cyclic substitutents are substitutents such as R whose meaning is described for formula (Ia).

R' may also represent a carbocyclic radical which is saturated or contains 1 or 2 unsaturations in the cycle, generally containing 3 to 8 carbon atoms, preferably 6 carbon atoms in the cycle: the cycle may be substituted with substitute such as R.

R' may also represent an aromatic carbocyclic radical, preferably a monocyclic radical generally containing at least 4 carbon atoms, preferably 6 carbon atoms in the cycle; the cycle may be substituted with substitutents such as R.

The process of the invention is particularly applicable to aromatic ethers with formula (I) where R' represents a linear or branched alkyl radical containing 1 to 4 carbon atoms or a phenyl radical.

Examples of preferred radicals R' of the invention are methyl and ethyl.

In general formula (I) for aromatic ethers, residue A may represent the residue of a monocyclic aromatic carbocyclic compound containing at least 4 carbon atoms, preferably 6 carbon atoms, or the residue of a polycyclic carbocyclic compound which may be constituted by at least 2 aromatic carbocycles and form between them ortho- or ortho- and pericondensed systems or by at least 2 carbocylces of which at least one is aromatic and forming between them ortho- or ortho- and pericondensed systems. A particular example is a naphthalenic residue.

Residue A may carry one or more substitutents on the aromatic nucleus.

Examples of substitutents R are given below, but this list is not limiting. Any substitutent can be present on the cycle provided that it does not interfere with production of the desired product.

Since residue A may carry several alkoxy groups, the process of the invention can be used to acylate polyalkoxylated compounds.

The process of the invention is particularly applicable to aromatic ethers with formula (Ia):

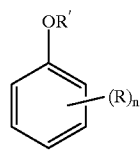

(Ia)

where:
n is a number less than or equal to 4, preferably 1 or 2;
radical R' represents a linear or branched alkyl radical containing 1 to 6 carbon atoms, preferably 1 to 4 carbon atoms, such as methyl, ethyl, propyl, isopropyl, butyl, isobutyl, sec-butyl, tert-butyl or a phenyl radical;
radical(s) R represent one of the following atoms or groups:
  a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
  a linear or branched alkenyl radical containing 2 to 6 carbon atoms, preferably 2 to 4 carbon atoms, such as vinyl, allyl;
  a cyclohexyl or benzyl radical;
  a linear or branched alkoxy radical containing 1 to 6 carbon atoms, preferably 1 to 4 carbon atoms, such as a methoxy, ethoxy, propoxy, isopropoxy or butoxy radical;
  an acyl group containing 2 to 6 carbon atoms:
  a radical with formula:
    —$R_1$—OH
    —$R_1$—$COOR_2$
    —$R_1$—CHO
    —$R_1$—$NO_2$
    —$R_1$—CN
    —$R_1$—N—$(R_2)_2$
    —$R_1$—CO—N—$(R_2)_2$
    —$R_1$—X
    —$R_1$—$CF_3$
      where $R_1$ represents a valence bond or a, saturated or unsaturated, linear or branched divalent hydrocarbon radical containing 1 to 6 carbon atoms such as methylene, ethylene, propylene, isopropylene, or isopropylidene; $R_2$ represents a hydrogen atom or a linear or branched alkyl radical containing 1 to 6 carbon atoms; and X represents a halogen atom, preferably a chorine, bromine or fluorine atom;
radicals R' and R and the 2 successive atoms of the benzene ring may form between them a cycle containing 5 to 7 carbon atoms, which may contain a further heteroatom.

When n is greater than or equal to 1, radicals R' and R and the 2 successive atoms of the benzene ring can be bonded together by an alkylene, alkenylene or alkenylidene radical containing 2 to 4 carbon atoms to form a saturated, unsaturated or aromatic heterocycle containing 5 to 7 carbon atoms. One or more carbon atoms may be replaced by a further heteroatom, preferably oxygen. Thus radicals OR' and R may represent a dioxymethylene or a dioxyethylene radical.

In formula (Ia), R' preferably represents a linear or branched alkyl radical containing 1 to 4 carbon atoms, preferably a methyl or ethyl radical.

The aromatic ether with formula (I) may carry one or more R substitutents.

More preferably, R represents one of the following atoms or groups:
  a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
  a linear or branched alkoxy radical containing 1 to 6 carbon atoms, preferably 1 to 4 carbon atoms, such as a methoxy, ethoxy, propoxy, isopropoxy, butoxy, isobutoxy, sec-butoxy or tert-butoxy radical;
  a halogen atom, preferably a fluorine, chlorine or bromine atom, or a trifluoromethyl radical.

In formula (Ia), R preferably represents a linear or branched alkoxy radical containing 1 to 4 carbon atoms, preferably a methoxy or ethoxy radical.

The process of the invention is particularly applicable to substituted aromatic ethers, i.e., to aromatic ethers with formula (I) or (Ia) where n is at least equal to 1.

Preferably, aromatic ethers with formula (I) or (Ia) are used in which:
n is at least equal to 1;
R' represents a linear or branched alkyl radical containing 1 to 6 carbon atoms or a phenyl radical;
R represents a linear or branched alkoxy radical containing 1 to 4 carbon atoms, preferably a methoxy or ethoxy radical;
radicals OR' and R form a dioxymethylene or dioxyethylene radical.

More particularly, the process of the invention is applicable to aromatic ethers with formula (Ia) where n equals 1, and radicals R and OR' both represent alkoxy radicals which may be identical or different.

Particular illustrations of compounds with formula (I) are: unsubstituted monoethers such as anisole, ethoxybenzene (phenetole), propoxybenzene, isopropoxybenzene, butoxybenzene, isobutoxybenzene, 1-methoxynaphthalene, 2-methoxynaphthalene, 2-ethoxynaphthalene; substituted monoethers such as 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-benzylanisole, 2-cyclohexylanisole, 1-bromo-2-ethoxybenzene, 1-bromo-3-ethoxybenzene, 1-chloro-2-ethoxybenzene, 1-chloro-3-ethoxybenzene, 1-ethoxy-2-ethylbenzene, 1-ethoxy-3-ethylbenzene, 1-methoxy-2-allyloxybenzene, 2,3-dimethylanisole, and 2,5-dimethylanisole;

diethers such as veratrol, 1,3-dimethoxybenzene, 1,4-dimethoxybenzene, 1,2-diethoxybenzene, 1,3-diethoxybenzene, 1,2-dipropoxybenzene, 1,3-dipropoxybenzene, 1,3-dipropoxybenzene, 1,2-methylenedioxybenzene, and 1,2-ethylenedioxybenzene; triethers such as 1,2,3-trimethoxybenzene, 1,3,5-trimethoxybenzene and 1,3,5-triethoxybenzene.

The compounds for which the process of the invention is particularly applicable are substituted ethers with formula (I) or (Ia) where n is at least equal to 1. The invention is well suited to the acylation of veratrol.

The acylation reactant is selected from the group formed by carboxylic acid halides and carboxylic acid anhydrides.

The carboxylic acids are saturated or unsaturated, linear or branched aliphatic carboxylic acids or saturated or unsaturated cycloaliphatic acids which may be substituted.

In particular, they have the following formula (II):

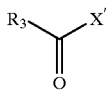

(II)

where:
$R_3$ represents:
 a saturated or unsaturated, linear or branched aliphatic radical containing 1 to 24 carbon atoms; or a saturated or unsaturated, monocyclic or polycyclic cycloaliphatic radical containing 3 to 12 carbon atoms;
X' represents:
 a halogen atom, preferably a chlorine or bromine atom;
 a —O—CO—$R_4$ radical where $R_4$, which may be identical or different to $R_3$, has the same meaning as $R_3$; $R_3$ and $R_4$ may together form a saturated or unsaturated, linear or branched aliphatic radical containing at least 2 carbon atoms.

More preferably, $R_3$ represents a linear or branched alkyl radical containing 1 to 12 carbon atoms, preferably 1 to 6 carbon atoms: the hydrocarbon chain may be interrupted by a heteroatom (for example oxygen), a functional group (for example —CO—) and/or may carry substitutents (for example halogen atoms or a $CF_3$ group).

$R_3$ also represents an alkenyl radical containing 2 to 10 carbon atoms, such as vinyl, propenyl, butenyl, pentenyl, hexenyl, octenyl or decenyl.

Radical $R_3$ also represents a non aromatic radical, preferably a cycloaliphatic radical, for example a cyclohexyl radical, which may be substituted. Any substitutent can be present on the ring provided that it does not interfere with production of the desired product.

Particular examples of substitutents are:
 a linear or branched alkyl radical containing 1 to 6 carbon atoms, preferably 1 to 4 carbon atoms, such as methyl, ethyl, propyl, isopropyl, butyl, isobutyl, sec-butyl or tert-butyl;
 a linear or branched alkoxy radical containing 1 to 6 carbon atoms, preferably 1 to 4 carbon atoms, such as a methoxy, ethoxy, propoxy, isopropoxy, butoxy, isobutoxy, sec-butoxy or tert-butoxy radical;
 a hydroxy group;
 a halogen atom, preferably a fluorine, chlorine or bromine atom.

Preferred acylation agents are acid anhydrides. In particular, they have formula (II) where $R_3$ and $R_4$ are identical and represent an alkyl radical containing 1 to 4 carbon atoms, which may carry halogen atoms, preferably chlorine.

When the acylation agent is an acid halide, it preferably has formula (II) where X' represents a chlorine atom and $R_3$ represents an alkyl radical containing 1 to 4 carbon atoms, preferably methyl or ethyl, and may carry halogen atoms, preferably chlorine.

Particular illustrative examples of acylation agents with formula (II) are:
acetic anhydride;
propanoic anhydride;
isobutyric anhydride;
trifluoroacetic anhydride;
monochloroacetyl anhydride;
dichloroacetyl anhydride;
acetyl chloride;
monochloroacetyl chloride;
dichloroacetyl chloride;
isobutanoyl chloride;
propanoyl chloride;
pivaloyl chloride;
crotonyl chloride.

In accordance with the invention, the acylation reaction is advantageously carried out in the liquid phase comprising the aromatic ether and the acylation agent in the presence of catalyst.

One of the starting reactants can act as the reaction solvent, but it is also possible to use an organic solvent.

Particular examples of suitable solvents are aliphatic or aromatic hydrocarbons which may or may not be halogenated, aliphatic, cycloaliphatic or aromatic ether-oxides, or polar aprotic solvents.

Particular examples of aliphatic or cycloaliphatic hydrocarbons are paraffins, in particular hexane, heptane, octane, nonane, decane, undecane, dodecane, tetradecane or cyclohexane, and aromatic hydrocarbons, in particular benzene, toluene, xylenes, cumene, and petroleum cuts constituted by a mixture of alkylbenzenes, in particular Solvesso® type cuts.

Particular examples of aliphatic or aromatic halogenated hydrocarbons are perchlorinated hydrocarbons, in particular tetrachloroethylene, hexacloroethane; partially chlorinated hydrocarbons such as dicloromethane, chloroform, 1,2-dicloroethane, 1,1,1-trichloroethane, 1,1,2,2-tetrachloroethane, pentachloroethane, trichloroethylene, 1-clorobutane, 1,2-dichlorobutane; monoclorobenzene, 1,2-dichlorobenzene, 1,3-dichlorobenzene, 1,4-dichlorobezene, 1,2,4-trichlorobenzene or mixtures of different chlorobenzes; bromoform, bromoethane or 1,2-dibromoethane; monobromobenzene or mixtures of monobromobenzene with one or more dibromobenezenes: and 1-bromonaphthalene.

Aliphatic, cycloaliphatic or aromatic ether-oxides can also be used as organic solvents, more particularly diethyl oxide, dipropyl oxide, diisopropyl oxide, dibutyl oxide, methyltertiobutylether, dipentyl oxide, diisopentyl oxide, ethyleneglycol dimethyl ether (1,2-dimethoxyethane), diethyleneglycol dimethylether (1,5-dimethoxy-3-oxapentane); biphenyl or benzyl oxide; dioxane, and tetrahydrofuran (THF).

Particular examples of polar aprotic solvents which can also be used in the process of the invention are linear or cyclic carboxamides such as N,N-dimethylacetamide (DMAC), N,N-diethylacetamide, dimethylformamide (DMF), diethylformamide or 1-methyl-2-pyrrolidinone (NMP); dimethylsulphoxide (DMSO); cyclic or non cyclic sulphones such as tetramethylsulphone, or dimethylsulphone; hexamethylphosphotriamide (HMPT); and cyclic or non cyclic tetrasubstituted ureas such as dimethylethyleneurea, dimethylpropyleneurea, and tetramethylurea.

Preferred solvents are: dichloromethane, tetrachloromethane, THF and diethyl oxide.

A mixture of organic solvents can also be used.

Preferably, the starting substrate is used as the reaction solvent.

As mentioned above, the aromatic ether is reacted with an acylation agent, optionally in the presence of a reaction solvent as defined above and in the presence of a solid catalyst as defined above.

The ratio between the number of moles of aromatic ether and the number of moles of acylation agent can vary since the substrate may act as the reaction solvent. Thus the ratio can be between 0.1 and 20, preferably between 0.5 and 10.

The quantity of catalyst used can vary between wide limits.

When the process is carried out batchwise, the catalyst can represent 0.01% to 50% by weight, preferably 1.0% to 20%, by weight with respect to the aromatic ether used. When the process is carried out continuously, however, for example by reacting a mixture of aromatic ether and acylation agent on a fixed catalyst bed, catalyst/aromatic ether ratios do not make sense and at a given instant, there may be an excess by weight of catalyst with respect to the starting aromatic ether.

The quantity of organic solvent used is generally selected so that the ratio between the number of moles of organic solvent and the number of moles of aromatic ether preferably varies between 0 and 100, more preferably between 0 and 50.

It is also possible to carry out the process of the invention in the presence of water: this latter can represent 0% to 10% by weight of acylation agent.

The temperature at which the acylation reaction is carried out depends on the reactivity of the starting substrate and that of the acylation agent.

It is between 20° C. and 300° C., preferably between 40° C. and 200° C.

The reaction is generally carried out at atmospheric pressure but lower pressures or higher pressures may also be suitable. The pressure is autogenous when the reaction temperature is higher than the boiling point of the reactants and/or products.

The process can be carried out batchwise or continuously.

In the first variation, there are no constraints on using the reactants. They can be introduced in any order.

After bringing the reactants into contact, the reaction mixture is brought to the desired temperature.

In the other variation, the reaction is carried out continuously in a tube reactor comprising the solid catalyst disposed in a fixed bed.

The aromatic ether and the acylation agent can be introduced into the reactor separately or as a mixture.

They can also be introduced into a solvent as mentioned above.

The residence time for the material stream on the catalytic bed varies, for example, between 15 minutes and 10 hours, preferably between 30 minutes and 5 hours.

At the end of the reaction, a liquid phase is obtained comprising the acylated aromatic ether which can be recovered conventionally, by distillation or recrystallisation from a suitable solvent, after elimination of excess reactants.

The process of the invention is particularly suitable for the preparation of 3,4-dimethoxyacetophenone, known as acetoveratrol, by the acetylation of veratrol.

One advantage of the process of the invention is that the acylation reaction takes place without O-dealkylation of the starting aromatic ether.

The following examples illustrate the invention without in any way limiting its scope.

Examples 2 to 4, 9 and 10 are comparative examples.

The yields given in the examples are defined as follows:

Yield: $RR_{AA}$=number of moles of acylation agent introduced/number of moles of acylated aromatic compound formed %

EXAMPLE 1

In this example, a catalyst of the invention was prepared in which the active phase was a Y zeolite of structural type FAU with a lattice parameter a=24.29 Ångström and with the following characteristics:

a global Si/Al ratio of 15.2:

a framework Si/Al ratio of 20;

a $Na/Al^{IV}$ atomic ratio of 0.018.

The ratio $Na/Al^{IV}$ was determined with respect to the aluminium ($Al^{IV}$) present in the zeolite framework and assuming that all the sodium was in the cationic position.

Acetylation of Veratrol 5.5 g of veratrol (40 mmole), 1.1 g of acetic anhydride and 0.11 g of zeolite which had been calcined at 550° C. in a stream of dry air were charged into a closed 30 ml reactor.

The reactor was then heated to 90° C.

After 6 hours, the reaction mixture was filtered then analysed by gas chromatography.

The catalytic results are shown in Table (I).

EXAMPLE 2*

In this example, which is given by way of illustration, the active phase was a ZSM-5 zeolite of structural type MFI with a global Si/Al ratio of 27.

Acetylation of Veratrol

Veratrol acylation was carried out under the operating conditions described for Example 1. The catalytic results are shown in Table (I).

EXAMPLE 3*

In this comparative example, the active phase was a mordenite zeolite of structural type MOR with a global Si/Al ratio of b 100.

Acetylation of Veratrol

Veratrol acylation was carried out under the operating conditions described for Example 1. The catalytic results are shown in Table (I).

EXAMPLE 4*

In this comparative example, the active phase was a beta zeolite of structural type BEA with a global Si/Al ratio of 12.5.

Acetylation of Veratrol

Veratrol acylation was carried out under the operating conditions described for Example 1. The catalytic results are shown in Table (I).

TABLE (I)

| Example no | Catalyst | Global Si/Al ratio | $RR_{AA}$ (%) |
|---|---|---|---|
| 1 | H-Y | 15.2 | 95 |
| 2* | HZSM5 | 27 | 12 |
| 3* | H-mordenite | 100 | 25 |
| 4* | Hβ | 12.5 | 53 |

Table 1 shows the importance of using a catalyst of the invention, namely a Y zeolite which can produce a high yield of acetoveratrol.

EXAMPLE 5

In this example, a catalyst was prepared which was in accordance with the invention.

20 g of a Y zeolite in its Na form, with a global Si/Al ratio of 2.8 was suspended in 100 ml of an aqueous 10 N ammonium nitrate ($NH_4NO_3$) solution.

The suspension was heated under reflux for 3 hours.

The zeolite was separated by filtering and washed in distilled water. This cycle of operations was carried out 4 times in succession.

A $NH_4$—Y zeolite was obtained which was calcined at 725° C. in the presence of steam in a fixed bed for 4 hours.

It was then suspended in 100 ml of a 2 N nitric acid solution and the mixture was heated under reflux for 2 hours.

The zeolite was separated by filtering and washed with distilled water until a wash water was obtained with a pH equivalent to that of distilled water.

The characteristics of the dealuminised H—Y zeolite obtained are shown in Table (II).

Acetylation of Veratrol 5.5g of veratrol (40 mmole), 1.1 g of acetic anhydride and 0.11 g of zeolite which had been calcined at 550° C. in a stream of dry air were charged into a closed 30 ml reactor.

The reactor was then heated to 90° C.

After 6 hours, the reaction mixture was filtered then analysed by gas chromatography.

The catalytic results are shown in Table (III).

EXAMPLE 6

In this example, a catalyst was prepared which was in accordance with the invention.

20 g of a Y zeolite in its Na form with a global Si/Al ratio of 2.8 was suspended in 100 ml of an aqueous 10 N ammonium nitrate ($NH_4NO_3$) solution.

The suspension was heated under reflux for 4 hours.

The zeolite was separated by filtering and washed in distilled water.

The Y zeolite had a sodium content of 2.4% by weight.

A partially exchanged Y zeolite was obtained which was calcined at 725° C. in the presence of steam in a fixed bed for 4 hours.

It was then suspended in 100 ml of a 1.2 N nitric acid solution and the mixture was heated under reflux for 2 hours.

The zeolite was separated by filtering and washed with distilled water until a wash water was obtained with a pH equivalent to that of distilled water.

It then underwent three ion exchange runs using 10 N ammonium nitrate solutions using the same procedure as that described at the start of the operation.

The characteristics of the dealuminised H—Y zeolite obtained are shown in Table (II).

Acetylation of Veratrol

Veratrol acylation was carried out under the operating conditions described for Example 5. The results are shown in Table (III).

EXAMPLE 7

In this example, a catalyst was prepared which was in accordance with the invention.

20 g of a Y zeolite in its Na form with a global Si/Al ratio of 2.7 was suspended in 100 ml of an aqueous 10 N ammonium nitrate ($NH_4NO_3$) solution.

The suspension was heated under reflux for 3 hours.

The zeolite was separated by filtering and washed in distilled water. This cycle of operations was carried out 4 times in succession.

A $NH_4$—Y zeolite was obtained which was calcined at 750° C. in the presence of steam in a fixed bed for 4 hours.

It was then suspended in 100 ml of a 2.5 N nitric acid solution and the mixture was heated under reflux for 3 hours.

The zeolite was separated by filtering and washed with distilled water until a wash water was obtained with a pH equivalent to that of distilled water.

The characteristics of the dealuminised H—Y zeolite obtained are shown in Table (II).

Acetylation of Veratrol

Veratrol acylation was carried out under the operating conditions described for Example 5. The results are shown in Table (III).

EXAMPLE 8

In this example, a catalyst was prepared which was in accordance with the invention.

20 g of a Y zeolite in its Na form with a global Si/Al ratio of 2.7 was suspended in 100 ml of an aqueous 10 N ammonium nitrate ($NH_4NO_3$) solution.

The suspension was heated under reflux for 3 hours.

The zeolite was separated by filtering and washed in distilled water. This cycle of operations was carried out 4 times in succession.

A $NH_4$—Y zeolite was obtained which was calcined at 770° C. in the presence of steam in a fixed bed for 4 hours.

It was then suspended in 100 ml of a 1.5 N nitric acid solution and the mixture was heated under reflux for 3 hours.

The zeolite was separated by filtering and washed with distilled water until a wash water was obtained with a pH equivalent to that of distilled water.

Acid attack was then carried out using a 2 N nitric acid solution under the same operating conditions as those described above.

The characteristics of the dealuminised H—Y zeolite obtained are shown in Table (II).

Acetylation of Veratrol

Veratrol acylation was carried out under the operating conditions described for Example 5. The results are shown in Table (III).

EXAMPLE 9*

In this example, given by way of comparison, the Y zeolite used was provided by PQ Zeolites, reference number CBV50001.

The characteristics of this H—Y zeolite, determined by the same analytical methods as those used to characterise the zeolites of Examples 1 to 8, are shown in Table (II).

Acetylation of Veratrol

Veratrol acylation was carried out under the operating conditions described for Example 5. The results are shown in Table (III).

EXAMPLE 10*

In this example, given by way of comparison, the Y zeolite used was provided by Degussa, reference number TC134.

The characteristics of this H—Y zeolite, determined by the same analytical methods as those used to characterise the zeolites of Examples 1 to 9, are shown in Table (II).

TABLE (II)

| Example No | Lattice parameter a (Angström) | Global Si/Al atomic ratio (FX) | Framework Si/Al$^{(IV)}$ | Na/Al$^{(IV)(3)}$ (atomic %) |
|---|---|---|---|---|
| 5 | 24.29 | 13.5 | 29$^{(1)}$ | 5.7 |
| 6 | 24.35 | 5.5 | 13.6$^{(1)}$ | 2.3 |
| 7 | 24.26 | 17.8 | 27$^{(2)}$ | 1.9 |
| 8 | 24.26 | 33.8 | 45$^{(1)}$ | 2.2 |
| 9* | 24.53 | 3.3 | 4.8$^{(1)}$ | 1.4 |
| 10* | 24.29 | 11.6 | 23$^{(2)}$ | 26.2 |

$^{(1)}$The framework Si/Al$^{(IV)}$ ratio was determined by X ray diffraction. This technique measured the lattice parameter of the Y zeolite then the Fichter-Schmittler relationship (H. Fichter-Schmittler, U. Loshe, G. Engelhardt, and V. Patzelova, Cryst. Res. Tech. 1984, 19, Kl) was used to obtain the framework Si/Al$^{(IV)}$ ratio.
$^{(2)}$The framework Si/Al(IV) ratio was determined by $^{29}$Si NMR of the solid and by infrared spectroscopy.
$^{(3)}$The Na/Al$^{(IV)}$ ratio was determined with respect to the aluminium [Al$^{(IV)}$] present in the framework and assuming that all the sodium was in the cationic position.

Acetylation of Veratrol 5.5 g (40 mmole) of veratrol, 1.1 g (11 mmole) of acetic anhydride and 0.11 g of a catalyst described in Examples 5 to 10 were charged into a closed 30 ml reactor.

The reactor was then heated to 90° C.

After 6 hours, the reaction mixture was filtered then analysed by gas chromatography.

The catalytic results are shown in Table (III).

TABLE (III)

| Catalyst reference | RR$_{AA}$ (%) |
|---|---|
| Example 5 | 89 |
| Example 6 | 95 |
| Example 7 | 97 |
| Example 8 | 91 |
| Example 9* | 22 |
| Example 10* | 36 |

EXAMPLE 11

This example used the Y zeolite described in Example 5.
Acetylation of Anisole 5.81 g (53 mmole) of anisole, 1g (10.7 mmole) of acetic anhydride and 0.11 g of catalyst were charged into a closed 30 ml reactor.

The reactor was then heated to 90° C.

After 6 hours, the reaction mixture was filtered then analysed by gas chromatography.

The yield of 4-methoxyacetophenone (acetoanisole) was:

RR$_{AA}$=69%.

What is claimed is:

1. A process for the acylation of an aromatic ether which comprises reacting said ether with an acylation agent in the presence of a zeolitic catalyst, said acylation reaction being carried out in the presence of an effective quantity of a catalyst comprising a faujasite type zeolite or a Y zeolite with the following physico-chemical characteristics:
    an atomic ratio denoted "global Si/Me$^1$" between the number of atoms of the element silicon and the number of atoms of every trivalent element Me$^1$ contained in the zeolite in the range 2.4 to 90;
    an Me$^2$ alkali metal content such that the atomic ratio Me$^2$/Me$^{1(IV)}$ between the number of atoms of alkali metal Me$^2$ and the number of atoms of every trivalent element Me$^{1(IV)}$ included in the zeolitic network is less than 0.2; and
    an atomic ratio denoted the "Si/Me$^{1(IV)}$ of the zeolitic framework" between the number of atoms of the element silicon and the number of atoms of every trivalent element Me$^{1(IV)}$ included in the zeolitic network in the range 5 to 100.

2. A process according to claim 1, wherein the atomic ratio denoted "global Si/Me$^1$" is in the range 2.4 to 60.

3. A process according to claim 1, wherein the atomic ratio Me$^2$/Me$^{1(IV)}$ is less than 0.05.

4. A process according to claim 1, wherein the number of atoms is in the range 8 to 60.

5. A process according to claim 1, wherein the aromatic ether has general formula (I):

(I)

wherein:
    A represents the residue of a cycle forming all or a portion of a monocyclic or polycyclic aromatic carbocyclic system containing at least one OR' group, A optionally carrying one or more substitutents;
    R represents one or more identical or different substitutents;
    R' represents a saturated or unsaturated hydrocarbon radical containing 1 to 24 carbon atoms, a linear or branched acyclic aliphatic radical; a monocyclic or polycyclic, saturated, unsaturated or aromatic cycloaliphatic radical; or a saturated or unsaturated, linear or branched aliphatic radical carrying a cyclic substitutent;
    R' and R optionally forming a cycle optionally containing a further heteroatom; and
    n is a number less than or equal to 4.

6. A process according to claim 1, wherein R' represents:
    a saturated or unsaturated, linear or branched acyclic aliphatic radical containing 1 to 12 carbon atoms, the hydrocarbon chain being optionally interrupted by a heteroatom, a functional group or carrying a substitutent;
    a saturated or unsaturated, linear or branched acyclic aliphatic radical carrying a cyclic substitutent optionally substituted, said acyclic radical being bonded to the cycle by a valence bond, a heteroatom or a functional group;
    a carbocyclic radical which may be saturated or contain 1 or 2 unsaturations in the cycle, containing 3 to 8 carbon atoms, said cycle being optionally substituted; and
    an aromatic carbocyclic radical, containing at least 4 carbon atoms, said aromatic carbocyclic radical being optionally substituted.

7. A process according to claim 1, wherein R' represents a linear or branched alkyl radical containing 1 to 4 carbon atoms or a phenyl radical.

8. A process according to claim 6, wherein the residue A represents the residue of a monocyclic aromatic carbocyclic compound containing at least 4 carbon atoms or the residue of a polycyclic carbocyclic compound, residue A optionally carrying one or more substitutents on the aromatic residue.

9. A process according to claim 1, wherein the aromatic ether has formula (Ia):

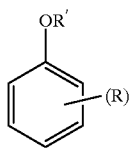

(Ia)

where:
n is a number less than or equal to 4;
radical R' represents a linear or branched alkyl radical containing 1 to 6 carbon atoms or a phenyl radical;
radical(s) R is selected from the group consisting of:
  a linear or branched alkyl radical containing 1 to 6 carbon atoms;
  a linear or branched alkenyl radical containing 2 to 6 carbon atoms;
  a linear or branched alkoxy radical containing 1 to 6 carbon atoms;
  a cyclohexyl or benzyl radical;
  an acyl group containing 2 to 6 carbon atoms; and
  a radical with formula selected from the group consisting of:
    —$R_1$—OH,
    —$R_1$—COO$R_2$,
    —$R_1$—CHO,
    —$R_1$—NO$_2$,
    —$R_1$—CN,
    —$R_1$—N—($R_2$)$_2$,
    —$R_1$—CO—N—($R_2$)$_2$,
    —$R_1$—X, and
    —$R_1$—CF$_3$,
    wherein $R_1$ represents a valence bond or a saturated or unsaturated, linear or branched divalent hydrocarbon radical containing 1 to 6 carbon atoms; $R_2$ represents a hydrogen atom or a linear or branched alkyl radical containing 1 to 6 carbon atoms; and X represents a halogen atom; and
radicals R' and R and the 2 successive atoms of the benzene ring optionally forming between them a cycle containing 5 to 7 carbon atoms, optionally containing a further heteroatom.

10. A process according to claim 9, wherein n is greater than or equal to 1, radicals R and R' and the 2 successive atoms of the benzene ring can be bonded together by an alkylene, alkenylene or alkenylidene radical containing 2 to 4 carbon atoms to form a saturated, unsaturated or aromatic heterocycle containing 5 to 7 carbon atoms in which one or more carbon atoms can be replaced by a heteroatom, the radicals OR' and R optionally forming a dioxymethylene or dioxyethylene radical.

11. A process according to claim 5, wherein:
n is at least equal to 1;
R' represents a linear or branched alkyl radical containing 1 to 6 carbon atoms or a phenyl radical;
R represents a linear or branched alkoxy radical containing 1 to 4 carbon atoms;
radicals OR' and R optionally forming a dioxymethylene or dioxyethylene radical.

12. A process according to claim 9, wherein:
n is at least equal to 1;
R' represents a linear or branched alkyl radical containing 1 to 6 carbon atoms or a phenyl radical;

R represents a linear or branched alkoxy radical containing 1 to 4 carbon atoms;
radicals OR' and R optionally forming a dioxymethylene or dioxyethylene radical.

13. A process according to claim 9, wherein n equals 1 and radicals R and OR' both represent alkoxy radicals which may be identical or different.

14. A process according to claim 9, wherein said aromatic ether is veratrol.

15. A process according to claim 1, wherein the acylation agent has formula (II):

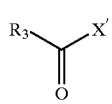

(II)

wherein:
$R_3$ represents:
  a saturated or unsaturated, linear or branched aliphatic radical containing 1 to 24 carbon atoms; or a saturated or unsaturated, monocyclic or polycyclic cycloaliphatic radical containing 3 to 12 carbon atoms;
X' is selected from the group consisting of:
  a halogen atom;
  a —O—CO—$R_4$ radical wherein $R_4$, which may be identical or different to $R_3$, has the same meaning as $R_3$; $R_3$ and $R_4$ optionally forming together a saturated or unsaturated, linear or branched aliphatic radical containing at least 2 carbon atoms.

16. A process according to claim 15, wherein X' represents a chlorine atom and $R_3$ represents a linear or branched alkyl radical containing 1 to 12 carbon atoms, the hydrocarbon chain being optionally interrupted by a heteroatom or by a functional group or optionally carrying halogen atoms; or X' represents a —O—CO—$R_4$ radical, where $R_3$ and $R_4$ are identical and represent an alkyl radical containing 1 to 4 carbon atoms optionally carrying halogen atoms.

17. A process according to claim 15, wherein the acylation agent is selected from the group consisting of:
  acetic anhydride;
  propanoic anhydride;
  isobutyric anhydride;
  trifluoroacetic anhydride;
  monochloroacetyl anhydride;
  dichloroacetyl anhydride;
  acetyl chloride;
  monochloroacetyl chloride;
  dichloroacetyl chloride;
  propanoyl chloride;
  isobutanoyl chloride;
  pivaloyl chloride; and
  crotonyl chloride.

18. A process according to claim 1, wherein the catalyst is a Y zeolite or a faujasite type zeolite having, in its dehydrated state, a chemical composition corresponding to the following empirical formula:

$$(1-x)H_2O, x[(Me^2)_2O],[(Me^1)_2O_3], 2nSiO_2$$

wherein:
Me$^1$ represents an element with a degree of oxidation of +3;

Me² represents a metal selected from the group of elements from column 1a and mixtures thereof;

n, equal to the "global Si/Me¹" atomic ratio is in the range 2.4 to 90; and x, equal to the Me²/Me¹$^{(IV)}$ ratio defined above, is less than 0.2.

19. A process according to claim 18, wherein the catalyst is a zeolite with chemical formula (I) where Me¹ represents aluminium and Me² represents sodium or potassium or a mixture thereof.

20. A process according to claim 17, wherein the zeolite has a lattice parameter α of less than 24.50 Angström, preferably in the range 24.23 to 24.42 Angström.

21. A process according to claim 1, wherein the Y zeolite undergoes dealuminising treatment so that the Si/Me¹ atomic ratios are greater than 2.4.

22. A process according to claim 1, wherein the dealuminising treatment comprising one of the following steps: calcining in the presence of vapour, calcining in the presence of steam followed by attack with mineral acids, dealuminising using reactants selected from the group consisting of silicon tetrachloride ($SiCl_4$), ammonium hexafluorosilicate (($NH_4)_2SiF_6$), ethylenediaminetetracetic acid (EDTA) and mono or disodium form of EDTA and direct acid attack using solutions of mineral acids or organic acids.

23. A process according to claim 1, wherein the zeolite is used alone or mixed with a mineral matrix which is selected from the group consisting of metal oxides, aluminium oxides, silicon oxides, zirconium oxides, clays, kaolin, talc and montmorillonite.

24. A process according to claim 1, further comprising the use of an organic solvent selected from the group consisting of:

aliphatic, cycloaliphatic or aromatic hydrocarbons;

aliphatic or aromatic halogenated hydrocarbons;

aliphatic, cycloaliphatic or aromatic ether-oxides;

linear or cyclic carboxamides;

dimethylsulphoxide (DMSO);

cyclic sulphones;

non cyclic sulphones;

hexamethylphosphotriamide (HMPT);

cyclic tetrasubstituted ureas; and non cyclic tetrasubstituted ureas.

25. A process according to claim 1, wherein the ratio between the number of moles of aromatic ether and the number of moles of acylation agent is between 0.1 and 20.

26. A process according to claim 1, wherein the quantity of catalyst represents 0.01% to 50% by weight of the aromatic ether employed.

27. A process according to claim 1, wherein the temperature at which the acylation reaction is carried out is between 20° C. and 300° C.

* * * * *